United States Patent
Farley (10) Patent No.: US 10,251,782 B2
(45) Date of Patent: Apr. 9, 2019

(54) VITRECTOMY PROBE WITH A COUNTERBALANCED ELECTROMAGNETIC DRIVE

(71) Applicant: Novartis AG, Basel (CH)

(72) Inventor: Mark Farley, Laguna Hills, CA (US)

(73) Assignee: Novartis AG, Basel (CH)

( * ) Notice: Subject to any disclaimer, the term of this patent is extended or adjusted under 35 U.S.C. 154(b) by 1107 days.

(21) Appl. No.: 14/526,718

(22) Filed: Oct. 29, 2014

(65) Prior Publication Data

US 2016/0120697 A1 May 5, 2016

(51) Int. Cl.
| | | |
|---|---|---|
| *A61F 9/007* | (2006.01) | |
| *H02K 33/16* | (2006.01) | |
| *A61B 17/00* | (2006.01) | |
| *A61B 17/32* | (2006.01) | |

(52) U.S. Cl.
CPC ......... *A61F 9/00763* (2013.01); *H02K 33/16* (2013.01); *A61B 17/32002* (2013.01); *A61B 2017/00141* (2013.01); *A61B 2017/00398* (2013.01); *A61B 2017/00876* (2013.01)

(58) Field of Classification Search
CPC ........... A61F 9/00763; A61B 17/32002; A61B 2017/00876; A61B 2017/00398; A61B 2017/320032; A61B 2017/00141; H02K 33/16

See application file for complete search history.

(56) References Cited

U.S. PATENT DOCUMENTS

| | | | |
|---|---|---|---|
| 2,707,389 A | 5/1955 | Fortier | |
| 3,646,727 A | 3/1972 | Wachsmuth | |
| 3,776,238 A | 12/1973 | Peyman et al. | |
| 4,099,529 A | 7/1978 | Peyman | |

(Continued)

FOREIGN PATENT DOCUMENTS

| | | |
|---|---|---|
| CN | 101425733 A | 5/2009 |
| CN | 201766481 U | 3/2011 |

(Continued)

OTHER PUBLICATIONS

International Searching Authority, International Search Report and Written Opinion, PCT/US2014/064547, dated Feb. 4, 2015, 11 pages.

(Continued)

*Primary Examiner* — Todd Scherbel
*Assistant Examiner* — Brooke Labranche (57) ABSTRACT

According to one example, an ophthalmic surgical probe for treating an eye of a patient includes a body arranged for grasping by a surgeon and a cutting element extending distally from the body. The cutting element includes a sleeve member and an inner member disposed within the sleeve member, the inner member being movable axially with respect to the sleeve member. The probe also includes an actuating element configured to reciprocally move the inner member relative to the sleeve member. The actuating element includes a first coil secured within the body, a first magnet operatively secured to the inner member, and a second magnet that is not secured to the inner member, the second magnet being positioned and arranged to move in an opposite direction of the first magnet upon application of a voltage to the first coil.

14 Claims, 6 Drawing Sheets

(56) References Cited

U.S. PATENT DOCUMENTS

| | | |
|---|---|---|
| 4,314,560 A | 2/1982 | Helfgott et al. |
| 4,476,532 A | 10/1984 | Akiyama et al. |
| 4,533,890 A | 8/1985 | Patel |
| 4,840,111 A | 6/1989 | Garnjost |
| 4,940,468 A | 7/1990 | Petillo |
| 5,275,607 A | 1/1994 | Lo et al. |
| 5,587,536 A | 12/1996 | Rasmussen |
| 5,643,304 A | 7/1997 | Schechter et al. |
| 5,716,363 A | 2/1998 | Josephberg |
| 5,720,742 A | 2/1998 | Zacharias |
| 5,829,335 A | 11/1998 | Ewald et al. |
| 5,846,257 A | 12/1998 | Hood |
| 5,868,728 A | 2/1999 | Giungo et al. |
| 5,979,494 A | 11/1999 | Perkins et al. |
| 5,989,262 A | 11/1999 | Josephberg |
| 6,051,011 A | 4/2000 | Weidenbenner |
| 6,059,792 A | 5/2000 | Josephberg |
| 6,221,038 B1 | 4/2001 | Brisken |
| 6,450,966 B1 | 9/2002 | Hanna |
| 6,527,736 B1 | 3/2003 | Attinger et al. |
| 6,575,990 B1 | 6/2003 | Wang et al. |
| 6,773,445 B2 | 8/2004 | Finlay et al. |
| 7,335,217 B2 | 2/2008 | Wang et al. |
| 8,038,692 B2 | 10/2011 | Valencia et al. |
| 9,101,442 B2 | 8/2015 | McDonell |
| 2002/0173814 A1 | 11/2002 | Jung et al. |
| 2003/0078482 A1 | 4/2003 | Kenan |
| 2003/0195538 A1 | 10/2003 | Wang et al. |
| 2004/0049217 A1 | 3/2004 | Ross et al. |
| 2004/0227604 A1 | 11/2004 | Mitteer et al. |
| 2008/0172077 A1 | 7/2008 | Valencia et al. |
| 2008/0188881 A1 | 8/2008 | Chon |
| 2008/0208233 A1 | 8/2008 | Barnes et al. |
| 2009/0203480 A1 | 8/2009 | Petzold et al. |
| 2009/0259242 A1 | 10/2009 | Gerg et al. |
| 2010/0241125 A1 | 9/2010 | Termanini |
| 2011/0144641 A1 | 6/2011 | Dimalanta, Jr. et al. |
| 2013/0038145 A1 | 2/2013 | Fujiwara |
| 2013/0144317 A1 | 6/2013 | Valencia |
| 2014/0062224 A1* | 3/2014 | Kim ............... H02K 33/16 310/15 |
| 2015/0157503 A1 | 6/2015 | Chon |

FOREIGN PATENT DOCUMENTS

| | | |
|---|---|---|
| CN | 103944346 A | 7/2014 |
| DE | 10247869 A1 | 5/2004 |
| DE | 10247869 B4 | 2/2007 |
| EP | 0469641 B1 | 6/1989 |
| EP | 0356372 A2 | 2/1990 |
| EP | 0626628 A1 | 11/1994 |
| EP | 0626628 B1 | 12/1997 |
| EP | 1110520 A1 | 6/2001 |
| GB | 2018601 A | 10/1979 |
| GB | 2063579 A | 6/1981 |
| JP | 2002335662 A | 11/2002 |
| SU | 835 436 A1 | 6/1981 |
| WO | 93/05718 A1 | 4/1993 |
| WO | 93/05719 A1 | 4/1993 |
| WO | 00/78371 A1 | 12/2000 |
| WO | 2002/041788 A1 | 5/2002 |
| WO | 2008/000599 A1 | 1/2008 |
| WO | 2008/097755 A2 | 8/2008 |
| WO | 2008/097755 A3 | 10/2008 |
| WO | 2015/084541 A1 | 6/2015 |
| WO | 2016/069277 A1 | 5/2016 |

OTHER PUBLICATIONS

International Searching Authority, International Search Report and Written Opinion, PCT/US2015/055698, dated Jan. 11, 2016, 12 pages.

* cited by examiner

VITRECTOMY PROBE WITH A COUNTERBALANCED ELECTROMAGNETIC DRIVE

BACKGROUND

The present disclosure relates generally to ophthalmic surgical probes. More particularly, but not by way of limitation, the present disclosure pertains to an electromagnetically driven vitrectomy probe.

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibrils that are often attached to the retina. Therefore, cutting and removal of the vitreous must be done with great care to avoid traction on the retina, the separation of the retina from the choroid, a retinal tear, or, in the worst case, cutting and removal of the retina itself. Delicate operations such as mobile tissue management (e.g., cutting and removal of vitreous near a detached portion of the retina or a retinal tear), vitreous base dissection, and cutting and removal of membranes are particularly difficult.

The use of microsurgical cutting probes in posterior or anterior segments ophthalmic surgery is well known. Such vitrectomy probes are typically inserted via an incision at the cornea or in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Standard vitrectomy probes typically include a hollow needle that acts as a sleeve piece with a port on the end to pull in vitreous fibrils. An inner member, placed within the hollow needle, moves back and forth to open and close the port. This operates to cut any fibrils that enter the port while it is open.

Pneumatic mechanisms are typically used to drive commercially available vitrectomy probes. Pneumatic mechanisms, however, have various limitations. First, pneumatic mechanisms are limited in the speed at which they can operate. Accordingly, high cut rates may be limited using probes relying on pneumatic actuation due to the mechanical actuation that must occur based on a compressible gas. Second, pneumatic mechanisms tend to be noisy, which can be annoying to surgeons and other health care providers during a surgical procedure. One alternative to a pneumatic driving mechanism is an electromagnetic driving mechanism. But, conventional electromagnetic mechanisms may be noisy and produce unwanted vibration as the magnets within the vitrectomy probe rapidly move back and forth. Thus, there is a need for continued improvement in the use and operability of vitrectomy probes. The probes discussed herein are arranged to address one or more of the deficiencies in the prior art.

SUMMARY

This disclosure relates generally to, and encompasses, apparatuses and methods for removing fluid from the eye, and more specifically to ophthalmic surgical systems with vitrectomy probes and methods of using the systems to remove fluid from the eye.

According to one example, an ophthalmic surgical probe for treating an eye of a patient includes a body arranged for grasping by a surgeon and a cutting element extending distally from the body. The cutting element includes a sleeve member and an inner member disposed within the sleeve member, the inner member being movable axially with respect to the sleeve member. The probe also includes an actuating element configured to reciprocally move the inner member relative to the sleeve member. The actuating element includes a first coil secured within the body, a first magnet operatively secured to the inner member, and a second magnet that is not secured to the inner member, the second magnet being positioned and arranged to move in an opposite direction of the first magnet upon application of a voltage to the first coil.

An ophthalmic surgical system includes a probe. The probe includes a body arranged for grasping by a surgeon and a cutting element extending distally from the body. The cutting element includes a sleeve member and an inner member disposed within the sleeve member, the inner member being movable axially with respect to the sleeve member. The probe also includes an actuating element configured to reciprocally move the inner member with respect to the sleeve member. The actuating element includes a first coil secured within the body and circumscribing the inner member, a first magnet operatively secured to the inner member, a second magnet that is not secured to the inner member, the second magnet being positioned such that corresponding poles of the first magnet and the second magnet face opposite directions. The system also includes a console that includes a voltage supply, the voltage supply being in electrical communication with the first coil.

A method for operating a vitrectomy probe includes applying a first voltage to a first coil within a body of the vitrectomy probe such that a first magnet is moved in a first direction and a second magnet is moved in a second direction that is opposite of the first direction, the first magnet being secured to an inner member positioned within a sleeve member such that reciprocal, axial movement of the inner member opens and closes a port at an end of the sleeve member. The method further includes applying a second voltage to the coil, the second voltage having a polarity that is opposite the first voltage, to cause the first magnet to move in the second direction and the second magnet to move in the first direction.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to apparatuses, systems, and methods for removing ocular tissue and/or fluid from the eye. The various figures show embodiments of exemplary ophthalmic surgical probes and methods of using the devices to remove ocular tissue and/or fluid from a patient's eye. Embodiments described herein incorporate a counterbalanced electromagnetic drive that allows for reduced vibration, thus enhancing the vitrectomy operation for a surgeon performing the operation. One of ordinary skill in the art, however, would understand that similar embodiments could be used to remove tissue and/or fluid from other locations in the body without departing from the general intent or teachings of the present disclosure.

Figure 1:
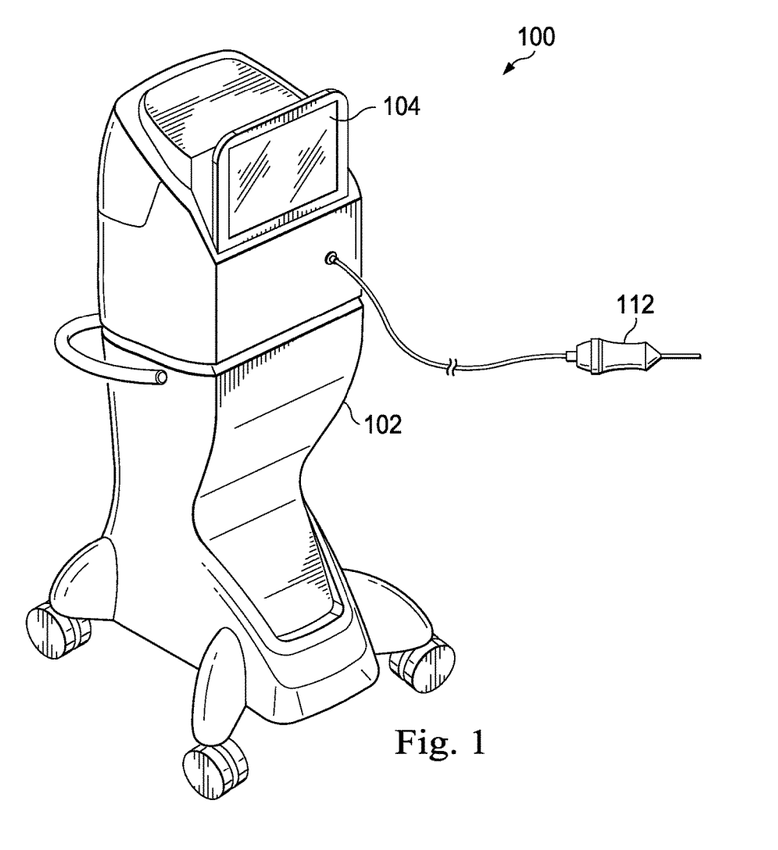
FIG. 1 is a diagram showing an illustrative ophthalmic surgical system with a vitrectomy probe according to one example incorporating the principles described herein.

FIG. 1 is a diagram showing an illustrative ophthalmic surgical system 100. According to the present example, the ophthalmic surgical system 100 includes a base housing 102 and an associated display screen 104 showing data relating to system operation and performance during a vitrectomy surgical procedure. In this exemplary embodiment, the base housing 102 is a mobile console that may be used by a health care provider to perform a vitrectomy surgical procedure. The ophthalmic surgical system 100 includes a vitrectomy probe 112 and is configured to be used during an ophthalmic surgical procedure, such as, for example, a vitrectomy surgical procedure. The base housing 102 may be configured to process, receive, and store data and provide signals to the vitrectomy probe and/or the display 104.

Figure 2:
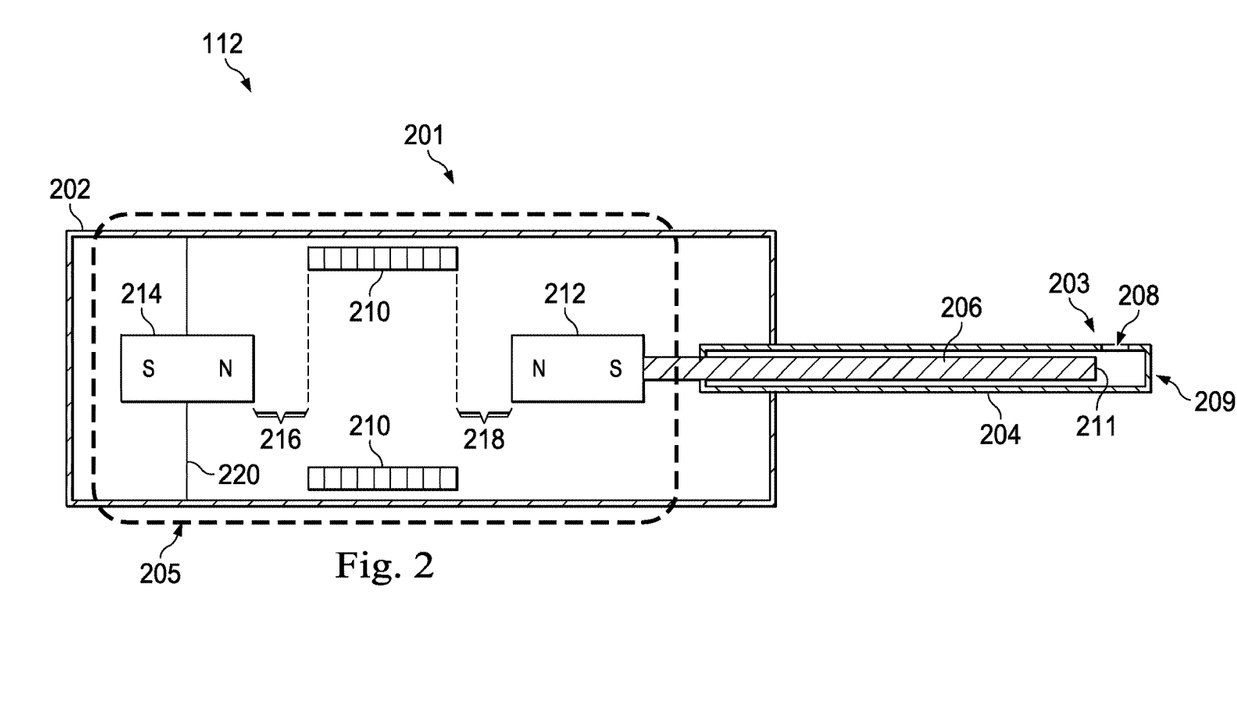
FIG. 2 is a diagram showing an illustrative longitudinal cross-sectional view of a vitrectomy probe with a counterbalanced electromagnetic drive according to one example incorporating the principles described herein.

FIG. 2 is a stylized diagram showing an illustrative longitudinal, cross-sectional view of a vitrectomy probe 112 with a counterbalanced electromagnetic drive 205. The counterbalanced electromagnetic drive 205 is housed within a body 201. The body 201 supports a cutting element 203 extending therefrom. The cutting element 203 is driven by the counterbalanced electromagnetic drive 205.

The body 201 forms a handle portion 202 that may be grasped and manipulated by a surgeon when performing a surgical procedure, such as a vitrectomy. In some embodiments, the exterior portion of the body 201 is ergonomically designed for comfortable grasping by the surgeon. The body 201 may be made from a variety of materials commonly used to form such tools. For example, the body 201 may be made of, for example, a lightweight aluminum, a polymer, or other material. Depending on the embodiment, it may be sterilized and used or reused in more than one surgical procedure, or it may be a single-use device. The inner portion of the body 201 is designed to house the counterbalanced electromagnetic drive 205. The inner portion of the body 201 also supports other features or elements of the probe 112.

Extending from the body 201 is the cutting element 203. The cutting element 203 is the portion of the probe 112 that interfaces with the patient. It is designed to penetrate a globe of an eye and may be used to remove vitreous or perform other functions or tasks. The cutting element 203 includes the inner member 206 and the sleeve member 204. The sleeve member 204 is a hollow needle designed to enter the patient's eye. The sleeve member 204 includes a port 208 at the distal end 209. The port 208 is disposed along the side of the distal end 209 as illustrated. The port 208 may be a square, rectangular, circular, elliptical, or other shaped opening. The opening is sized and shaped to allow vitreous fibrils from the patient's eye to enter. The inner member 206 axially moves within the sleeve member 204 to open and close the port 208, thereby cutting any vitreous fibrils that enter the port 208 while it is open.

The inner member 206 of the cutting element 203 operates as the cutter portion of the vitrectomy probe 112. Thus, the distal end 211 of the inner member 206 is sufficiently sharp so that it can cut the vitreous fibrils. The inner member 206 may be made from a variety of materials such as stainless steel, titanium, a biocompatible polymer, or other materials. In some cases, the inner member 206 may include multiple pieces attached together. For example, the distal end 211 of the inner member 206 may be a cutter piece made of a different material than the opposing proximal end. In some examples, the inner member 206 may be a hollow tube that is in fluid communication with an aspiration lumen (not shown). The aspiration lumen is in fluid connection with a suction mechanism to create a vacuum force. Thus, vitreous fibrils that are severed by the cutting element 203 can be aspirated through the aspiration lumen.

The counterbalanced electromagnetic drive 205 drives the cutting element 203. Specifically, the counterbalanced magnetic drive 205 moves the inner member 206 with respect to the sleeve member 204. The counterbalanced electromagnetic drive 205 includes at least one electromagnetic coil 210, a first magnet 212 that acts as a driving magnet, and a second magnet 214 that acts as a counterbalancing magnet.

The electromagnetic coil 210 may be formed by winding a conductive wire into a solenoid formation. When an electric current is applied to such a formation, a magnetic field is created in the center of the coil. The direction of the magnetic field is based on the direction of the electric current flowing through the wire. The electromagnetic coil 210 is fixedly secured within the body 201. In some examples, the electromagnetic coil 210 is positioned such that the center of the solenoid is aligned with the inner member 206. While only a single electromagnetic coil is illustrated in the cross-sectional view of FIG. 2, other embodiments may include additional coils.

The first magnet 212, which acts as a driving magnet, is secured to the inner member 206. Thus, movement of the first magnet 212 causes corresponding movement of the inner member 206. In this example, the first magnet 212 is a cylinder magnet that is secured to the proximal end of the inner member 206. In some examples, the first magnet 212 may be hollow such that the inner member can fit through the center of the first magnet 212. In such a case, the outer surface of the inner member 206 can be secured to the inner surface of the hollow magnet.

The second magnet 214 acts as a counterbalancing magnet. The second magnet 214 is not secured to the inner member 206. In some cases, the second magnet 214 may simply be unattached and free to move. For example, it may be disposed within a specifically designed chamber (not shown) that enables free cycling or oscillation. In some examples, however, the second magnet 214 may be suspended. In one example, a flex member 220 such as a flexible elastomeric membrane may be used to suspend the second magnet 214 while still permitting axial movement.

The second magnet 214 is positioned such that the poles of the second magnet 214 are in an opposite direction than the poles of the first magnet 212. In this example, the second magnet 214 is also a cylinder magnet. The second magnet 214 is in tandem and axially aligned to the first magnet 212. The second magnet 214 may also have similar magnetic properties to those of the first magnet 212. Additionally, the second magnet 214 has a substantially similar mass as the first magnet 212. Thus, when a current passes through the coil 210 and produces an electromagnetic force to cause the first magnet 212 to move in a specific direction, that same electromagnetic force will cause corresponding movement of the counterbalancing second magnet 214 in the opposite direction. The substantially equal and opposing movements of the two magnets 212, 214 can reduce the overall vibration of the vitrectomy probe 112 by producing substantially equally and opposing forces. In some examples, the masses and magnetic properties of the magnets can be tuned such that there is a balance in opposing forces resulting from movement of the magnets. This may account for friction, drag, or other features that may influence the balance of forces.

The electromagnetic force experienced by the magnets 212, 214 from the electromagnetic coil 210 is affected by the distance between the magnets 212, 214 and the electromagnetic coil 210. In some examples, the distance 216 between the second magnet 214 and the electromagnetic coil 210 may be substantially similar to the distance 218 between the first magnet 212 and the electromagnetic coil 210. In other examples, however, the distances 216, 218 may be tuned to best allow for counterbalancing while accounting for other factors such as frictional forces that affect movement of the magnets 212, 214.

Figure 3:
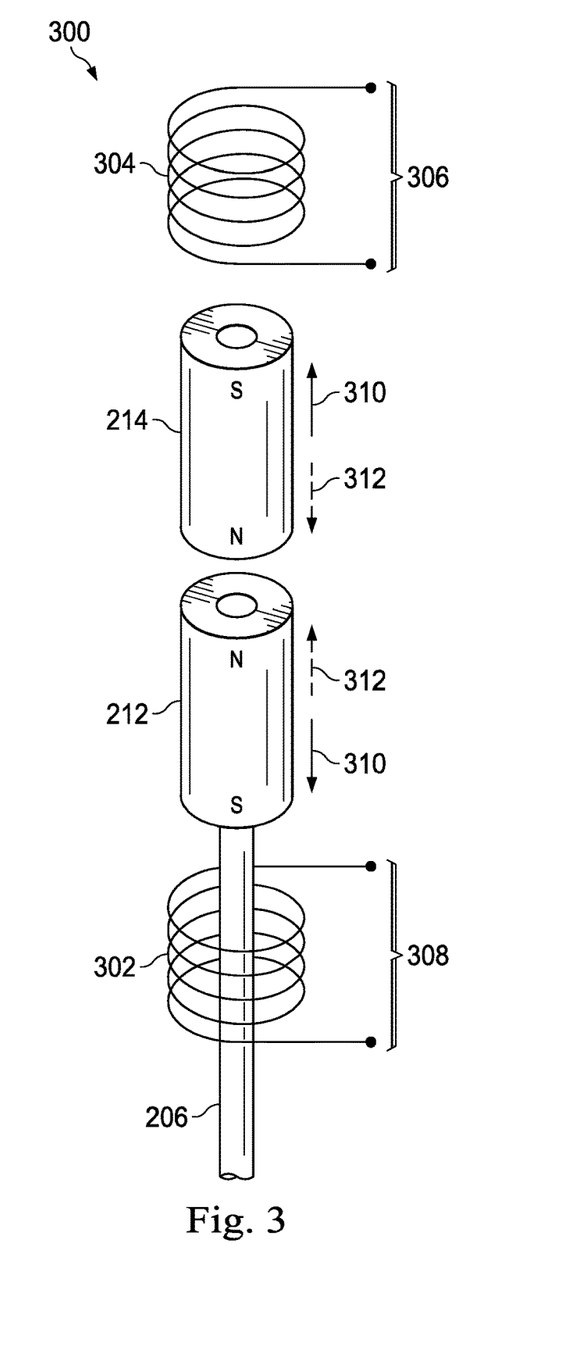
FIG. 3 is a diagram showing an illustrative perspective view of an actuation element for a vitrectomy probe with tandem magnets in the counterbalanced electromagnetic drive according to one example incorporating the principles described herein.

FIG. 3 is a diagram showing an illustrative perspective view of an actuation element 300 for a vitrectomy probe with tandem magnets 212, 214 in a counterbalanced electromagnetic drive. According to the present example, the actuation element 300 includes a first coil 302 and a second coil 304. The tandem magnets 212, 214 are placed between the two coils 302, 304.

The first coil 302 is in a distal position and the second coil 304 is in a proximal position. Both coils may be wound such that when a voltage having a particular polarity is applied to both coils 302, 304 (e.g., through ends 308, 306, respectively), the coils 302, 304 produce a magnetic force in the same direction. Because the two magnets 212, 214 are disposed with poles in opposite directions, the same magnetic force from both of the coils 302, 304 will cause the two magnets 212, 214 to move in different directions. For example, if a first voltage having a first polarity is applied to both coils 302, 304, then the first magnet 312 moves in a distal direction while the second magnet 214 moves in a proximal direction as indicated by the solid arrows 310. If a second voltage having a second polarity that is opposite the first polarity is applied to both of the coils 302, 304, then the first magnet 212 moves in the proximal direction while the second magnet 214 moves in the distal direction as indicated by the dashed arrows 312.

A voltage signal that rapidly alternates between voltages of different polarity may be applied to the electromagnetic coils 302, 304 so that both magnets 212, 214 move back and forth rapidly. Because the inner member 206 is secured to the first magnet 212, the inner member will also move back and forth rapidly to open and close the port (208, FIG. 2) and cut any vitreous fibrils that enter the port. The second magnet 214 moves to counterbalance the movement of the first magnet 212.

Figure 4:
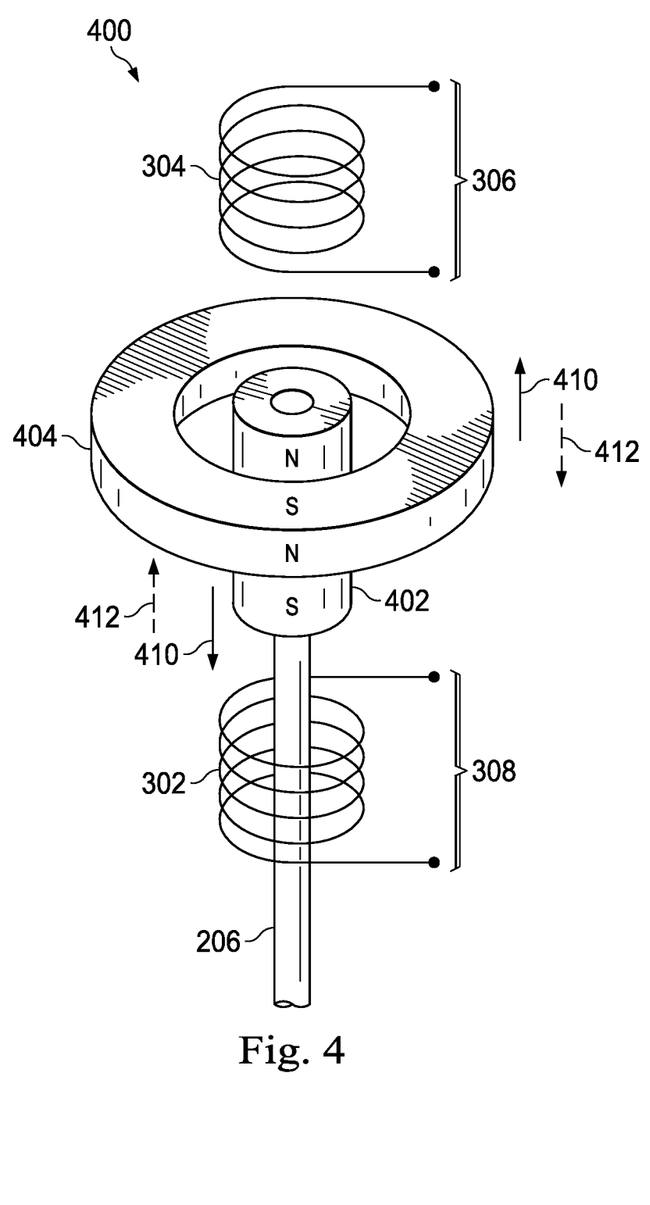
FIG. 4 is a diagram showing an illustrative perspective view of an actuation element for a vitrectomy probe with a circumscribing magnet in the counterbalanced electromagnetic drive according to one example incorporating the principles described herein.

FIG. 4 is a diagram showing an illustrative perspective view of an actuation element 400 for a vitrectomy probe with a circumscribing magnet 404 in a counterbalanced electromagnetic drive. According to the present example, the actuation element includes two coils 302, 304 and two magnets 402, 404. The first magnet 402 is secured to the inner member 206. The second magnet 404, which is the counterbalancing magnet, is a ring magnet that circumscribes the first magnet 402. The second magnet 404 is not secured to the inner member 206 and is does not make physical contact with the first magnet 402 and can thus move independently of the first magnet 402. The second magnet 404 may also be positioned so that it is concentric with the first magnet 402.

The second magnet 404 has poles that face opposite direction than the poles of the first magnet 402. Thus, when a voltage is applied to the coils 302, 304, a magnetic force from the coils will cause the first magnet 402 and the second magnet 404 to move in opposite directions. While having different shapes, the two magnets 402, 404 may have similar masses. The second magnet 404 is not secured to the inner member 206. The second magnet 404 may be unattached or suspended by a flex member (not shown).

Because the two magnets 402, 404 have poles in opposite directions, the same magnetic force from both of the coils 302, 304 will cause the two magnets 402, 404 to move in different directions. For example, if a first voltage having a first polarity is applied to both coils 302, 304, then the first magnet 402 moves in a distal direction while the second magnet 404 moves in a proximal direction as indicated by the solid arrows 410. If a second voltage having a second polarity that is opposite the first polarity is applied to both of the coils 302, 304, then the first magnet 212 moves in the proximal direction while the second magnet 214 moves in the distal direction as indicated by the dashed arrows 412.

A voltage signal that rapidly alternates between voltages of different polarity may be applied to the electromagnetic coils 302, 304 so that both magnets 402, 404 move back and forth rapidly. Because the inner member 206 is secured to the first magnet 402, the inner member will also move back and forth rapidly to open and close the port (208, FIG. 2) and cut any vitreous fibrils that enter the port. The second magnet 404 moves to counterbalance the movement of the first magnet 402, thereby reducing the vibration of the vitrectomy probe.

Figure 5:
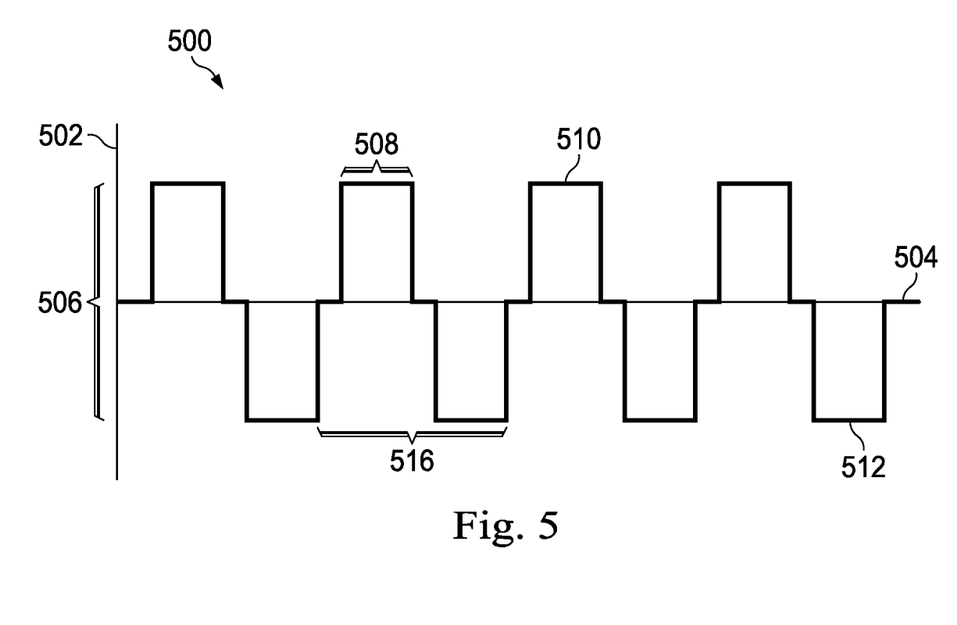
FIG. 5 is a diagram showing an illustrative electrical signal used to drive a counterbalanced electromagnetic probe according to one example of principles described herein.

FIG. 5 is a diagram showing an illustrative electrical signal 506 used to drive a counterbalanced electromagnetic probe. According to the present example, the vertical axis 502 represents the strength of a signal, such as in terms of voltage or current. The horizontal axis 504 represents time.

The signal 506 includes a series of positive pulses 510 and a series of negative pulses 512. The signal 506 alternates between the positive pulses 510 and the negative pulses. In this example, when the signal 506 is applied to one or more electromagnetic coils (210, 302, 304, FIGS. 2-4) as described above, the positive pulses will push the associated magnets (212, 214, 402, 404, FIGS. 2-4) in one direction while the negative pulses 512 will push the associated magnets (212, 214, 402, 404, FIGS. 2-4) in the opposite direction. For example, the positive pulses 510 may correspond to movement of the magnets 212, 214 as indicated by the solid arrows 310 in FIG. 3. Accordingly, the negative pulses 512 may correspond to movement of the magnets as indicated by the dashed arrows 312 in FIG. 3.

The electric signal 506 is a pulse waveform 500. The strength of the pulses 510, 512 may be based on the specifications of the electromagnetic coils such as the number of windings and gauge size, as well as the force needed to move the inner member (206, FIG. 2) as desired. The pulse width 508 may also be based on the force needed to move the inner member from one point to another. The width of the pulses may also be selected based on the force necessary to overcome the static friction between the inner member and the sleeve member (204, FIG. 2).

The wavelength 516 of the signal 506 is directly related to the frequency at which the signal 506 operates. The frequency may be adjusted to set the rate at which the probe cuts the vitreous fibrils. The rate may be defined as cuts per minute. For example, the frequency may be adjusted to set the probe to cut at a rate of 7,000 to 15,000 cuts per minute. In a more specific example, the vitrectomy probe 112 may be set to cut at a rate between about 9,000 to 12,000 cuts per minute, and more specifically, the vitrectomy probe 112 may operate at 10,000 cuts per minute. For example, to operate at 10,000 cuts per minute, the frequency of the signals is set to approximately 168 hertz (Hz).

Various other control signals may be used to drive the probe. For example, there may be two independent control signals for each of the two coils of the probe. Such control signals may be substantially coincident or opposite in phase. In some examples, the independent signals may have equal or opposite polarities. The two independent control signals may have overlapping duty cycles. The two independent control signals may be pulsed or may have pulsed width modulation (PWM). The control signals may have bipolar or unipolar waveforms. Other characteristics of the control signals that can effectively drive the probe using the counterbalancing principles described herein may be used.

Figure 6:
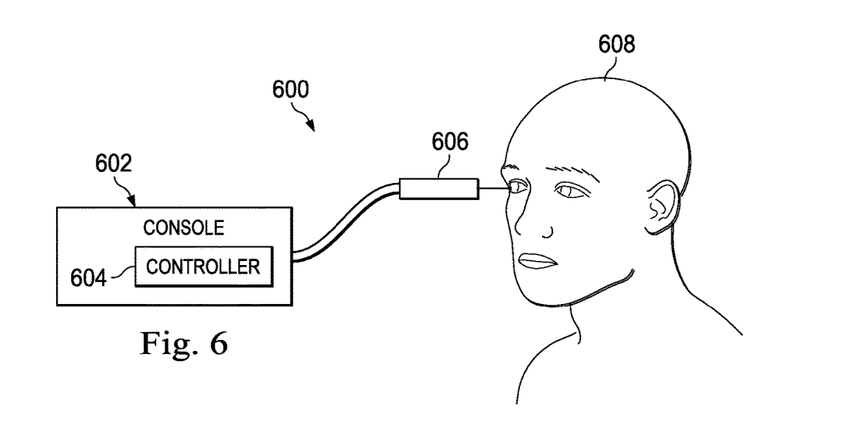
FIG. 6 is a diagram showing an ophthalmic surgical system with a counterbalanced vitrectomy probe performing a surgical procedure on a patient according to one example incorporating the principles described herein.

FIG. 6 is a diagram showing an ophthalmic surgical system 600 with a counterbalanced vitrectomy probe performing a surgical procedure on a patient. According to the present example, the system 600 includes a console 602 and a hand piece 606. The console 602 includes a controller 604. The hand piece 606 may be the same probe 112 discussed above, or may be another probe used by an operator or surgeon to treat a condition of the eye. In this example, the distal portion is inserted into the eye of a patient 608.

Many of the details of these components are unchanged from those described with reference to other embodiments, and those descriptions will not be repeated here. The console 602 includes components to drive and work with the hand piece 606. Additional components and features of the console 602 would be apparent to one of ordinary skill in the art. The controller 604 within the console 602 provides the desired electrical signals to the hand piece 606. These signals may be adjusted by the operator based on surgical parameters, surgeon preference, patient condition, or other factors related to the eye of the patient 608.

Figure 7:
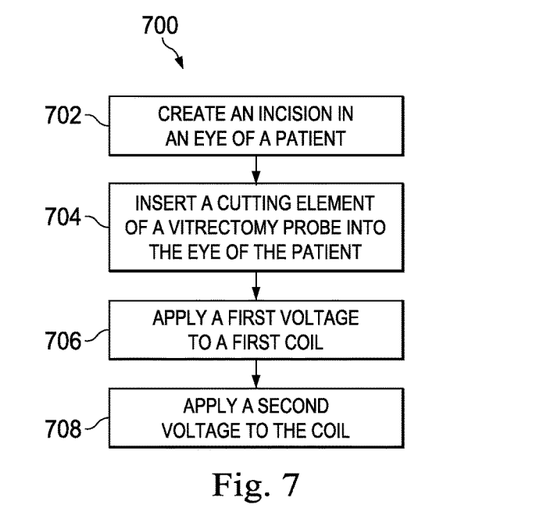
FIG. 7 is a flowchart showing an illustrative method for treating a patient with a vitrectomy probe having a counterbalanced electromagnetic drive according to one example incorporating the principles described herein.

FIG. 7 is a flowchart showing an illustrative method for treating a patient with a vitrectomy probe having a counterbalanced electromagnetic drive according to one example incorporating the principles described herein. According to the present example, the method 700 includes creating an incision in an eye of a patient at 702. At 704, the method 700 includes inserting a cutting element of a vitrectomy probe into the eye of the patient.

According to some examples, the probe includes a body and a cutting element extending distally from the body. The cutting element includes a sleeve member and an inner member disposed within the sleeve member. The inner member is movable with respect to the sleeve member. The cutting element also includes an actuating element that is configured to reciprocally move the inner member with respect to the sleeve member. The actuating element includes one or more coils secured within the body, a first magnet secured to the inner member, and a second counterbalancing magnet that is not secured to the inner member.

At 706, the method includes applying a first voltage to at least one coil within the body of the vitrectomy probe. The voltage causes the at least one coil to produce an electromagnetic field. Because the first and second magnets are disposed with polarities in opposite directions, the electromagnetic field causes the first magnet to move in a first direction and the second magnet to move in a second direction that is opposite of the first direction.

At 708, the method further includes applying a second voltage to the at least one coil. The second voltage has a polarity that is opposite the polarity of the first voltage. This causes the at least one coil to produce a different electromagnetic field that causes the first magnet to move in the second direction and the second magnet to move in the first direction. By alternatingly applying the first voltage and the second voltage, the inner member moves back and forth to open and close the port to sever vitreous fibrils that enter the port. With the cutting element in operation, the surgeon may complete a vitrectomy procedure by aspirating vitreous humor from the eye of the patient through the port in the needle. Vitreous that enters the port is severed and aspirated through the needle to the main housing, where the aspirated tissue will be collected in a disposal reservoir. When the procedure is complete, the needle is withdrawn from the patient's eye, and additional procedures, not involving the vitrectomy probe, may occur.

Because the embodiments disclosed herein have magnets disposed with poles in opposite directions, and have specifically tuned properties such as mass, the cycling magnets offset the forces that would otherwise result in vibration of the vitrectomy probe. The reduced vibration makes the vitrectomy probe easier to hold and carefully manipulate. This enables a surgeon or clinician to have increased control to perform sensitive procedures and may result in less physician fatigue. The counterbalanced magnetic drive may also allow for faster cut rates. All this leads to better patient outcome and surgical results.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic surgical probe for treating an eye of a patient, the probe comprising:
    a body arranged for grasping by a surgeon;
    a cutting element extending distally from the body including:
        a sleeve member;
        an inner member disposed within the sleeve member, the inner member being movable axially with respect to the sleeve member; and
    an actuating element configured to reciprocally move the inner member relative to the sleeve member, the actuating element comprising:
        a first coil secured within the body;
        a first magnet operatively secured to the inner member; and
        a second magnet that is not secured to the inner member, the second magnet being positioned and arranged to move in an opposite direction of the first magnet upon application of a voltage to the first coil.

2. The probe of claim 1, wherein the second magnet is attached to the body with a flex member.

3. The probe of claim 1, wherein the first magnet is a cylinder magnet secured to a proximal end of the inner member.

4. The probe of claim 1, wherein the second magnet is a cylinder magnet in tandem with the first magnet.

5. The probe of claim 1, wherein the first magnet and the second magnet have masses that are substantially the same.

6. The probe of claim 1, further comprising a second coil that is wound in a same orientation as the first coil, the second coil being placed proximal to the first magnet.

7. The probe of claim 1, wherein the first coil is in electrical communication with a voltage supply that is configured to apply alternating voltages to the coil.

8. The probe of claim 1, further comprising a second coil that is placed proximal to the first magnet, wherein a voltage supply is configured to apply a first signal to the first coil and a second signal to the second coil such that one of:
    the first signal and second signal are substantially coincident; or
    the first signal and second signal are opposite phase and have equal or opposite polarity.

9. An ophthalmic surgical system comprising:
    a probe including:
        a body arranged for grasping by a surgeon;
        a cutting element extending distally from the body including:
            a sleeve member;
            an inner member disposed within the sleeve member, the inner member being movable axially with respect to the sleeve member; and
        an actuating element configured to reciprocally move the inner member with respect to the sleeve member, the actuating element comprising:
            a first coil secured within the body and circumscribing the inner member;
            a first magnet operatively secured to the inner member; and
            a second magnet that is not secured to the inner member, the second magnet being positioned such that corresponding poles of the first magnet and the second magnet face opposite directions; and
    a console that includes a voltage supply, the voltage supply being in electrical communication with the first coil.

10. The system of claim 9, wherein the first magnet is a cylinder magnet.

11. The system of claim 9, wherein the second magnet is in tandem with the first magnet.

12. The system of claim 9, wherein the first magnet and the second magnet have masses that are substantially the same such that application of a voltage to the coil causes the first magnet and the second magnet to move in opposite directions with similar force.

13. The system of claim 9, wherein the sleeve member comprises a port at an end and the inner member is positioned such that reciprocal, axial movement of the inner member with respect to the sleeve member opens and closes the port.

14. The system of claim 9, wherein the voltage supply is configured to apply an alternating voltage to cause reciprocal motion of the inner member with respect to the sleeve member.

* * * * *